United States Patent [19]

Ondetti et al.

[11] 4,339,600
[45] Jul. 13, 1982

[54] COMPOUNDS FOR ALLEVIATING ANGIOTENSIN RELATED HYPERTENSION

[75] Inventors: Miguel A. Ondetti, Princeton; David W. Cushman, West Windsor, both of N.J.

[73] Assignee: E. R. Squibb & Sons, Inc., Princeton, N.J.

[21] Appl. No.: 877,197

[22] Filed: Feb. 13, 1978

Related U.S. Application Data

[60] Continuation-in-part of Ser. No. 773,864, Mar. 3, 1977, abandoned, which is a division of Ser. No. 684,606, May 10, 1976, Pat. No. 4,053,651.

[51] Int. Cl.$^3$ ............... C07C 153/09; C07C 149/437; C07C 149/243; C07C 149/247
[52] U.S. Cl. ............... 562/426; 260/455 R; 562/556; 562/557; 424/301; 424/319
[58] Field of Search ............ 260/534 S, 534 R, 534 C, 260/534 E, 534 G, 534 L, 534 M, 455 R; 562/556, 557, 426

[56] References Cited

U.S. PATENT DOCUMENTS

| | | | |
|---|---|---|---|
| 2,723,972 | 11/1955 | Herrick | 560/16 |
| 3,246,025 | 4/1966 | Mita | 260/534 S |
| 3,517,089 | 6/1970 | Newallis | 260/942 |
| 3,971,828 | 7/1976 | Mita | 260/534 S |
| 4,046,889 | 9/1977 | Ondetti | 260/293.85 |
| 4,053,651 | 10/1977 | Ondetti | 260/534 S |
| 4,081,399 | 3/1978 | Dear | 260/534S |
| 4,091,024 | 5/1978 | Ondetti | 260/534 S |
| 4,305,958 | 12/1981 | Fujita | 424/319 |

FOREIGN PATENT DOCUMENTS

| | | | |
|---|---|---|---|
| 2709820 | 9/1977 | Fed. Rep. of Germany | 260/534 S |
| 1491204 | 7/1967 | France | 260/534 S |

*Primary Examiner*—Michael L. Shippen
*Attorney, Agent, or Firm*—Lawrence S. Levinson; Donald J. Barrack

[57] ABSTRACT

Compounds for alleviating or reducing angiotensin related hypertension in hypertensive mammals comprising angiotensin converting enzyme inhibitors selected from a group of mercaptoacyl aminoacids.

21 Claims, No Drawings

COMPOUNDS FOR ALLEVIATING ANGIOTENSIN RELATED HYPERTENSION

This application is a continuation-in-part of application Ser. No. 773,864, filed Mar. 3, 1977, now abandoned, which is a division of application Ser. No. 684,606, filed May 10, 1976, now U.S. Pat. No. 4,053,651, issued Oct. 11, 1977.

BACKGROUND OF THE INVENTION AND PRIOR ART

Angiotensin II is a powerful vasoconstrictor agent that has been implicated as the main causative agent in the etiology of renovascular hypertension.

Angiotensin II is formed from angiotensin I by the action of angiotensin converting enzyme. Angiotensin I is a biologically inert decapeptide cleaved from the blood protein angiotensinogen by the action of the enzyme renin [Oparil et al. New England J. of Med., 291, 389–457 (1974)]. Angiotensinogen and renin are also biologically inert.

Angiotensin converting enzyme is also responsible for the inactivation of bradykinin, a vasodilator agent that has been implicated in the regulation of renal function [Erdös, Circulation Research 36, 247 (1975)].

Agents that inhibit angiotensin converting enzyme can therefore counteract the pressor effect of angiotensin I since this is due only to its conversion to angiotensin II. These agents can be used therapeutically in the treatment of forms of renovascular and malignant hypertension as well as other forms of angiotensin dependent hypertension [Gavras et al., New England J. of Med. 291, 817 (1974)].

According to Oparil et al, supra, angiotensin II has a major role in maintaining circulatory homeostasis in the sodium depleted animal, but in the normal animal on a normal salt intake, angiotensin II is not required for the acute maintenance of blood pressure. In a variety of conditions that stress the renin-angiotensin system, acute adminstration of an Angiotensin Converting Enzyme inhibitor or an angiotensin II blocker lowers blood pressure and causes a rise in plasma renin activity.

Certain mercaptoacyl amino acids have been disclosed in the literature. U.S. Pat. No. 3,246,025, Apr. 12, 1966, shows mercaptopropionyl glycine derivatives which are useful for strengthening function of the liver and as antidotes for such poisons as mercury and organoarsenic compounds. See also German Offenlegungsschrift No. 2,349,707. U.S. Pat. No. 3,897,480, July 29, 1957, shows N-(α-mercaptoacyl)amino acids useful for prophyaxis and therapy in treating a metabolic disorder, such as nosotoxicosis due to a heavy metal, radiation disorder, diabetes or hepatitis. U.S. Pat. No. 3,857,951, Dec. 31, 1974, shows the use of 2-mercaptopropionylglycine and its alkali metal salts in treating respiratory diseases.

It has been reported that 2-mercaptopropionylglycine, known as a liver protecting agent, produced lowering of the blood pressure upon intravenous injection to anesthetized normotensive rats [Schulze, Arzneim. Forsch. 22, 1433 (1972)], an unreliable model [Schwartz, Methods in Pharmacology, Vol. 1, 125 (1971); Berger, Selected Pharmacological Testing Methods, Vol. 3, 171, 194 (1968)]; while others have reported no noticeable effects on blood pressure, etc., [Fujimura et al., Nippon Yakurigaku Zasshi 60, 278–92 (1964)]. See also Ripa, Proc. Int. Symp. Thiola, Osaka, Japan 1970, p. 226–230, who reported that in normotensive rats α-mercaptopropionylglycine increases angiotensinogen and lowers renin blood levels by a feedback homeostatic mechanism.

It has now been found that certain mercapto acyl amino acids are angiotensin converting enzyme inhibitors and when administered to species of hypertensive mammals they reduce or relieve angiotensin related hypertension.

BRIEF SUMMARY OF THE INVENTION

This invention relates to certain compounds as well as a method for reducing or relieving angiotensin related hypertension in mammalian species. The method comprises administering to the hypertensive mammal an angiotensin converting enzyme inhibitor from the group consisting of compounds having the formula

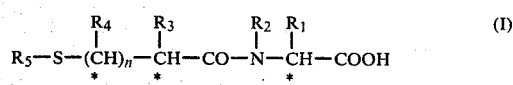

or a salt thereof.

$R_1$ is hydrogen, lower alkyl, phenyl-lower alkylene, hydroxy-lower alkylene, amino-lower alkylene, guanidino-lower alkylene, imidazolyl-lower alkylene, indolyl-lower alkylene, mercapto-lower alkylene, lower alkylmercapto-lower alkylene, carbamoyl-lower alkylene or carboxy-lower alkylene.

$R_2$, $R_3$ and $R_4$ each is hydrogen, lower alkyl or phenyl-lower alkylene;

$R_5$ is hydrogen, lower alkanoyl, benzoyl or

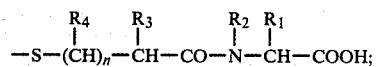

n is 0, 1 or 2.

The asterisks denote centers of asymmetry.

Compounds of formula I, and salts thereof, wherein n is 0; $R_1$ is hydroxy-lower alkylene, hydroxyphenyl-lower alkylene, amino-lower alkylene, guanidino-lower alkylene, imidazolyl-lower alkylene, indolyl-lower alkylene, mercaptolower alkylene, lower alkylmercapto-lower alkylene, carbamoyllower alkylene, or carboxy lower alkylene; and $R_2$, $R_3$, $R_4$ and $R_5$ each has the meaning defined above, compounds of formula I, and salts thereof, wherein n is 1; $R_1$ is lower alkyl, phenyl-lower alkylene, hydroxy-lower alkylene, hydroxyphenyl-lower alkylene, amino-lower alkylene, guanidino-lower alkylene, imidazolyl-lower alkylene, indolyl-lower alkylene, mercapto-lower alkylene, lower alkylmercapto-lower alkylene, carbamoyl-lower alkylene, or carboxy lower alkylene; $R_2$ and $R_3$ each is hydrogen, lower alkyl or phenyl-lower alkylene; $R_4$ is hydrogen; and $R_5$ has the meaning defined above, and compounds of formula I, and salts thereof, wherein n is 2 and $R_1$, $R_2$, $R_3$, $R_4$ and $R_5$ each has the meaning defined above, are new compounds. Members in the groups remaining are known.

DETAILED DESCRIPTION OF THE INVENTION

This invention comprises compounds and a method for the reduction or alleviation of renin-angiotensin related hypertension in mammals, such as rats, dogs, etc. Such renin-angiotensin related types of hypertension include, for example, renovascular hypertension and malignant hypertension. This invention therefore relates to the new compounds described above and to the method for relieving or alleviating renin-angiotensin related hypertension by the administration of a compound or compounds of formula I above. The method comprises the administration to the mammal suffering from renin-angiotensin related hypertension of an effective amount of an angiotensin converting enzyme inhibitor from the group consisting of compounds having formula I above.

The lower alkyl groups are straight or branched chain hydrocarbon radicals having up to seven carbon atoms like methyl, ethyl, propyl, isopropyl, butyl, isobutyl, t-butyl, pentyl, isopentyl, hexyl, heptyl and the like. The lower alkylene groups are of the same kind. The $C_1$-$C_4$ lower alkyl and lower alkylene groups and especially the $C_1$-$C_2$ lower alkyl and lower alkylene groups are preferred. The phenyl-lower alkylene groups include such lower alkylene groups having a phenyl group attached. Benzyl and phenethyl are especially preferred, most especially the former. The lower alkanoyl groups are the acyl radicals of the lower fatty acids like acetyl, propionyl, butyryl and the like. The $C_2$-$C_4$ members are preferred.

Compounds in the group represented by formula I which are derived from or include the structure of the amino acids alanine, leucine, phenylalanine, arginine, sarcosine, serine, asparagine, lysine, glutamine, histidine, tryptophane, cysteine, methionine, threonine, leucine, tyrosine, leucine, valine or aspartic acid are preferred, especially arginine. alanine, phenylalanine and leucine. $R_5$ is preferably hydrogen.

Experimental evidence indicates that $N^\alpha$-(3-mercapto-2-methylpropanoyl)-L-arginine, $N^\alpha$-(3-mercaptopropanoyl)-L-arginine, N-(3-mercaptopropanoyl)-L-phenylalanine and N-(3-mercaptopropanoyl-L-leucine are the most potent members of the group and they constitute an especially preferred group and especially preferred embodiments.

The compounds of formula I also form salts with various inorganic and organic bases which are also within the scope of the invention. Such salts include ammonium salts, alkali metal salts like sodium and potassium salts, alkaline earth metal salts, like calcium and magnesium salts, salts with organic bases, e.g., dicyclohexylamine, benzathine, hydrabamine and N-methyl-D-glucamine salts.

The compounds of this invention have one, two or three asymmetric carbons, if $R_1$, $R_2$ and $R_4$ are other than hydrogen. These carbons are indicated by an asterisk in formula I. The compounds accordingly exist in diastereoisomeric forms or in racemic mixtures thereof. All of these are within the scope of the invention.

It has been found that to attain a significant degree of biological activity the asymmetric carbon bearing the $R_1$ residue should be of the L-configuration, a stereospecificity that is not apparent in previously reported applications of mercapto acylamino acids. These accordingly are preferred.

The inhibition of the angiotensin converting enzyme by compounds of formula I can be measured in vitro with isolated angiotensin converting enzyme from rabbit lungs following the procedure described by Cushman and Cheung [Biochem. Pharmacol., 20, 1637 (1971)], and with an excised smooth muscle assay [E. O'Keefe, et al., Federation Proc. 31, 511 (1972)] in which these compounds have been shown to be powerful inhibitors of the contractile activity of angiotensin I and potentiators of the contractile activity of bradykinin.

By administering a composition containing one or a combination of the angiotensin converting enzyme inhibitor or physiologically acceptable salt thereof, to the hypertensive mammal suffering from angiotensin dependent hypertension, it intervenes in the renin→angiotensin I→angiotensin II sequence and the condition is reduced or alleviated.

A single dose, or preferably two or four divided daily doses, provided on a basis of about 1 to 1000 mg. per kilogram per day, preferably about 10 to 500 mg. per kilogram per day and especially 30 to 300 mg. per kilogram per day is appropriate to reduce angiotensin related elevated blood pressure. The animal model experiments described by S. L. Engel, T. R. Schaefer, M. H. Waugh and R. Rubin, Proc. Soc. Exp. Biol. Med. 143, 483 (1973) provide a valuable guide. The composition is preferably administered orally, but parenteral routes such as subcutaneously, intramuscularly, intravenously or intraperitoneally can also be employed.

The compounds of formula I can be prepared by several alternate procedures. A thio acid of the formula

$$R_6COSH \quad (II)$$

wherein $R_6$ is lower alkyl or phenyl, is made to react with an acrylic acid of the formula

$$\underset{CH_2=C-COOH}{\overset{R_3}{|}} \quad (III)$$

to obtain the product of the formula

$$R_6CO-S-CH_2-\underset{|}{\overset{R_3}{C}}H-COOH \quad (IV)$$

and this acid is coupled to the amino acid of the formula

$$\underset{HN-CH-COOH}{\overset{R_2 \ R_1}{| \ |}} \quad (V)$$

yielding a product of the formula

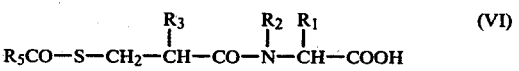
$$R_5CO-S-CH_2-\overset{R_3}{\underset{|}{C}}H-CO-\overset{R_2}{\underset{|}{N}}-\overset{R_1}{\underset{|}{C}}H-COOH \quad (VI)$$

which can then be converted to the product

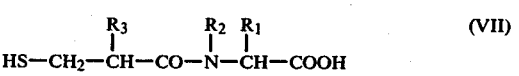
$$HS-CH_2-\overset{R_3}{\underset{|}{C}}H-CO-\overset{R_2}{\underset{|}{N}}-\overset{R_1}{\underset{|}{C}}H-COOH \quad (VII)$$

by ammonolysis.

In an alternate procedure, the amino acid of formula V is coupled with a haloalkanoic acid of the formula

$$X-(CH)_n-\overset{R_3}{\underset{|}{C}}H-COOH \quad (VIII)$$

wherein X is a halogen, preferably chlorine or bromine, by one of the known procedures in which the acid VIII is activated, prior to reaction with the amino acid V, involving formation of a mixed anhydride, symmetrical anhydride, acid chloride, active ester or the like. The product of this reaction is a compound of the formula

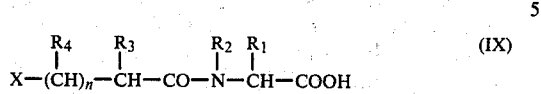

This product is subjected to a displacement reaction with the anion of a thioacid of formula II to give the compound of formula VI.

When $R_5$ in formula I is

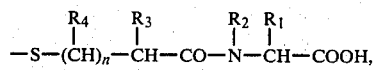

this product is a dimer of the formula

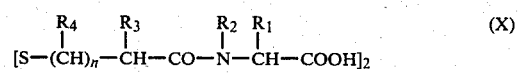

which is produced by oxidation of a compound of formula VII with an alcoholic solution of iodine. This product can also be obtained by treating the halo compound of formula IX with sodium disulfide.

The compounds of formula I are utilized to alleviate the angiotensin related hypertension by formulating in a composition such as tablet, capsule or elixir for oral administration. Sterile solutions or suspensions can be used for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharamceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention. Temperatures are in degrees celsius.

EXAMPLE 1

N-(3-Benzoylthiopropanoyl)-L-alanine

L-alanine (4.45 g.) is dissolved in aqueous N-sodium hydroxide (50 ml.) and the solution is chilled in the ice bath with stirring. 2 N sodium hydroxide (27 ml.) and 3-bromopropionyl chloride (8.5 g.) are added in that order and the mixture is removed from the ice bath and stirred at room temperature for three and one half hours. A mixture of thiobenzoic acid (7.5 g.) and potassium carbonate (4.8 g.) in water (50 ml.) is added and the mixture is stirred at room temperature overnight. After acidification with concentrated hydrochloric acid the aqueous solution is extracted with ethyl acetate, and the organic phase is washed with water dried and concentrated to dryness. The residue (14.9) is crystallized from ether to yield 7.1 g. of N-(3-benzoylthiopropanoyl)-L-alanine, m.p. 99°–100°.

EXAMPLE 2

N-(3-mercaptopropanoyl)-L-alanine

N-(3-benzoylthiopropanoyl)-L-alanine (4.2 g.) is dissolved in a mixture of water (7.5 ml.) and concentrated ammonium hydroxide (6 ml.). After one hour, the mixture is diluted with water, filtered and the filtrate is extracted with ethyl acetate. The aqueous phase is acidified with concentrated hydrochloric acid and extracted with ethyl acetate. The organic phase is washed with water, dried and concentrated to dryness in vacuo. The residue is crystallized from ethyl acetate-hexane to yield 1.87 g. of N-(3-mercaptopropanoyl)-L-alanine, m.p. 79°–81°.

EXAMPLE 3

N-(3-Benzoylthiopropanoyl)-L-leucine

By substituting L-leucine (6.55 g.) for the L-alanine in the procedure of Example 1, 16.7 g. of crude N-(3-benzoylthiopropanoyl)-L-leucine is obtained. This material is dissolved in a mixture of ethyl acetate (200 ml.) and dicyclohexylamine. The crystalline salt is filtered and dried. Yield 19.5 g., m.p. 178°–180°. This dicyclohexylammonium salt is treated with a mixture of ethyl acetate (200 ml.) and 10% aqueous potassium bisulfate (50 ml.). The organic phase is dried over magnesium sulfate, concentrated to dryness in vacuo and the residue crystallized from ethyl acetate-hexane to yield 8.8 g. of pure N-(3-benzoylthiopropanoyl)-L-leucine, m.p. 99°–101°.

EXAMPLE 4

N-(3-Mercaptopropanoyl)-L-leucine

By substituting N-(3-benzoylthiopropanoyl)-L-leucine (6.46 g.) for the N-(3-benzoylthiopropanoyl)-L-alanine in the procedure of Example 2, 2.75 g. of N-(3-mercaptopropanoyl)-L-leucine are obtained, m.p. 131°–132°. This material is recrystallized from acetonitrile.

EXAMPLE 5

N-(3-Benzoylthiopropanoyl)-L-Phenylalanine

By substituting L-phenylalanine (8.25 g.) for the L-alanine in the procedure of Example 1, 18.8 g. of crude N-(3-benzoylthiopropanoyl)-L-phenylalanine is obtained. This material is crystallized from acetonitrile to yield 11.1 g. of product, m.p. 123°–124°.

EXAMPLE 6

N-(3-Mercaptopropanoyl)-L-phenylalanine

N-(3-benzoylthiopropanoyl)-L-phenylalanine (1.78 g.) is dissolved in a mixture of water (20 ml.) and N sodium hydroxide (5.5 ml.). To this solution concentrated ammonium hydroxide (20 ml.) is added followed by water (20 ml.). After three hours, the reaction mixture is extracted with ethyl acetate, acidified with concentrated hydrochloric acid and reextracted with ethyl acetate. The second ethyl acetate extract is washed with water, dried over magnesium sulfate and concentrated to dryness in vacuo. The residue is chromatographed on a column of silica gel with a mixture of benzene-acetic acid to yield 0.47 g. of N-(3-mercaptopropanoyl)-L-phenylalanine, m.p. 106°–107°.

EXAMPLE 7

$N^\alpha$-(3-Benzoylthiopropanoyl)-L-arginine

L-arginine (8.7 g.) is dissolved in aqueous N sodium hydroxide (50 ml.) and the solution is chilled in the ice bath with stirring. 2 N sodium hydroxide (25 ml.) and 3-bromopropionyl chloride (8.5 g.) are added in that order and the mixture is removed from the ice bath and stirred at room temperature for 2 hours. A mixture of thiobenzoic acid (7.5 g.) and potassium carbonate (2.4 g.) in water (10 ml.) is added and the mixture is stirred overnight at room temperature. Ion-exchange resin [polystyrene sulfonic acid resin Dowex 50 (Mikes, Laboratory Handbook of Chromatographic Methods, Van Nostrand, 1961, page 256)] (100 ml.) is added and the suspension is applied to a column of the same resin (300 ml.). After washing off acidic materials with water, the $N^\alpha$-(3-benzoylthiopropanoyl)-L-arginine is eluted with a buffer of pyridine-acetic acid-water, pH 6.5. The fractions containing the desired material are pooled, concentrated to dryness and the residue is triturated with ether to yield 7 g., m.p. 345 (dec.).

EXAMPLE 8

$N^\alpha$-(3-mercaptopropanoyl)-L-arginine $N^\alpha$-(3-benzoylthiopropanoyl)-L-arginine (1 g.) is dissolved with vigorous stirring in a mixture of water (5 ml.) and concentrated ammonia (5 ml.). After one hour, the solution is extracted with ethyl acetate and concentrated to dryness in vacuo. The residue is chromatographed on a column of DEAE Sephadex [anion exchange resin derived from dextran (Mikes, supra, page 328)] (85 ml.) with a buffer of 0.005 M ammonium bicarbonate. The fractions containing the $N^\alpha$-(3-mercaptopropanoyl)-L-arginine (as indicated by positive thiol and Sakaguchi Reaction) are pooled and lyophilized to remove ammonium bicarbonate, yield 200 mg., m.p. 230° (starts decomposing at 200°).

EXAMPLE 9

N-(3-Benzoylthiopropanoyl)sarcosine

By substituting sarcosine (4.45 g.) for L-alanine in the procedure of Example 1, 7.9 g. of N-(3-benzoylthiopropanoyl)sarcosine, m.p. 139°–140° are obtained.

EXAMPLE 10

N-(3-Mercaptopropanoyl)sarcosine

By substituting N-(3-benzoylthiopropanoyl)sarcosine (2.8 g.) for N-(3-benzoylthiopropanoyl)-L-alanine in the procedure of Example 2, 1.65 g. of crude N-(3-mercaptopropanoyl)sarcosine is obtained. This material is converted to the dicyclohexylammonium salt (2.7 g.), m.p. 157°–158° and the purified salt is converted to the free acid by distribution between ethyl acetate and 10% potassium bisulfate.

EXAMPLE 11

N-(3-Mercaptopropanoyl)-L-serine

By substituting L-serine for the L-alanine in the procedure of Example 1, and then treating the product by the procedure of Example 2, N-(3-benzoylthiopropanol)-L-serine and N-(3-mercaptopropanoyl)-L-serine are obtained.

EXAMPLE 12

N-(3-Mercaptopropanoyl)-L-asparagine

By substituting L-asparagine for the L-alanine in the procedure of Example 1, and then treating the product by the procedure of Example 2, N-(3-benzoylthiopropanoyl)-L-asparagine and N-(3-mercaptopropanoyl)-L-asparagine are obtained.

EXAMPLE 13

$N^\alpha$-(3-Mercaptopropanoyl)-L-lysine

By substituting $N^\epsilon$-tert-butyloxycarbonyl-L-lysine [R. Schwyzer and W. Rittel, Helv. Chim. Acta 44, 159 (1961)] for L-alanine in the procedure of Example 1, and then treating the product by the procedure of Example 2, $N^\alpha$-(3-benzoylthiopropanoyl)-$N^\epsilon$-tert-butyloxycarbonyl-L-lysine and $N^\alpha$-(3-mercaptopropanoyl)-$N^\epsilon$-tert-butyloxycarbonyl-L-lysine are obtained. By treating this material with trifluoroacetic acid at room temperature for 15 minutes, $N^\alpha$-(3-benzoylthiopropanoyl)-L-lysine and $N^\alpha$-(3-mercaptopropanoyl)-L-lysine are obtained.

EXAMPLE 14

$N^\alpha$-(3-Mercaptopropanoyl)-L-histidine

By substituting L-histidine for the L-alanine in the procedure of Example 1, and then treating the product by the procedure of Example 2, $N^\alpha$-(3-benzoylthiopropanoyl)-L-histidine and $N^\alpha$-(3-mercaptopropanoyl)-L-histidine are obtained.

EXAMPLE 15

N-(3-Mercaptopropanoyl)glycine

By substituting glycine for the L-alanine in the procedure of Example 1, and then treating the product by the procedure of Example 2, (3-benzoylthiopropanoyl)glycine and N-(3-mercaptopropanoyl)glycine are obtained.

EXAMPLE 16

N-(3-Mercaptopropanoyl)-L-tryptophane

By substituting L-tryptophane for the L-alanine in the procedure of Example 1, and then treating the product by the procedure of Example 2, N-(3-benzoylthiopropanoyl)-L-tryptophane and N-(3-mercaptopropanoyl)-L-tryptophane are obtained.

EXAMPLE 17

N-(3-Mercaptopropanoyl)-L-cysteine

By substituting L-cysteine for the L-alanine in the procedure of Example 1, and then treating the product by the procedure of Example 2, N-(3-benzoylthiopropanoyl)-L-cysteine and N-(3-mercaptopropanoyl)-L-cysteine are obtained.

EXAMPLE 18

N-(3-Mercaptopropanoyl)-L-methionine

By substituting L-methionine for the L-alanine in the procedure of Example 1, and then treating the product by the procedure of Example 2, N-(3-benzoylthiopropanoyl)-L-methionine, and N-(3-mercaptopropanoyl)-L-methionine are obtained.

EXAMPLE 19

N-(3-Mercaptopropanoyl)-N-methyl-L-leucine

By substituting N-methyl-L-leucine for the L-alanine in the procedure of Example 1, and then treating the product by the procedure of Example 2, N-(3-benzoylthiopropanoyl)-N-methyl-L-leucine, and N-(3-mercaptopropanoyl)-N-methyl)-L-leucine are obtained.

EXAMPLE 20

$N^{\alpha}$-(3-Acetylthio-2-methylpropanoyl)-L-arginine

L-Arginine (2.61 g.) is dissolved in a mixture of sodium carbonate (3.2 g.) and water (30 ml.) and the solution is chilled in an ice bath. 3-Acetylthio-2-methylpropanoyl chloride (2.7 g.) is added and the reaction mixture is stirred at room temperature for 1.5 hours. Ion exchange resin (AG 50 W) 50 ml. is added and the suspension is applied to a column of the same resin (80 ml.). After washing with water, the $N^{\alpha}$-(3-acetylthio-2-methylpropanoyl)-L-arginine is eluted with a pyridine-acetic acid buffer pH 6.5, the solvent is removed in vacuo, the residue is dissolved in methanol and precipitated with ether to yield 3.86 g. of $N^{\alpha}$-(3-acetylthio-2-methylpropanoyl)-L-arginine, m.p. 133°.

EXAMPLE 21

$N^{\alpha}$-(3-Mercapto-2-methylpropanoyl)-L-arginine $N^{\alpha}$-(3-Acetylthio-2-methylpropanoyl)-L-arginine (1 g.) is dissolved in a mixture of water (5 ml.) and concentrated ammonia (5 ml.). After one hour at room temperature the solution is concentrated to 3 ml. in vacuo (no heat) and ion exchange resin AG-50 W is added until the pH of approximately 4. The suspension is applied to a column of the same resin and the $N^{\alpha}$-(3-mercapto-2-methylpropanoyl)-L-arginine is eluted with pyridine-acetate buffer pH 6.5. The solvent is removed in vacuo and the residue is freeze dried, yield 0.86 g., m.p. 100°.

EXAMPLE 22

N-(3-Acetylthio-2-methylpropanoyl)-L-valine

L-valine (88 g.) and sodium carbonate (40 g.) are dissolved in water (1 l.) and the solution is chilled in an ice bath with vigorous stirring. 3-Acetylthio-2-methylpropanoyl chloride (135 g.) and a solution of sodium carbonate (120 g.) in 500 ml. of water are added in five equal portions over a 15 minute period. After 1.5 hours the reaction mixture is extracted with ethyl acetate, the aqueous phase is acidified with concentrated hydrochloric acid and extracted with ethyl acetate. The organic phase is washed with water, dried over magnesium sulfate and concentrated to dryness to yield 190 g. of N-(3-acetylthio-2-methylpropanoyl)-L-valine.

EXAMPLE 23

N-(3-Mercapto-2-methylpropanoyl)-L-valine

N-(3-Acetylthio-2-methylpropanoyl)-L-valine (20 g.) is dissolved in a mixture of water (46 ml.) and concentrated ammonia (31 ml.). After one hour at room temperature the reaction mixture is extracted with ethyl acetate, the aqueous phase is acidified with concentrated hydrochloric acid and extracted with ethyl acetate. The organic phase is dried over magnesium sulfate and concentrated to dryness in vacuo to yield 19 g. of N-(3-mercapto-2-methylpropanoyl)-L-valine.

EXAMPLE 24

N-(3-Mercapto-2-methylpropanoyl)-L-phenylalanine

By substituting L-phenylalanine for the L-valine in the procedure of Example 22, and then treating the product by the procedure of Example 23, N-(3-acetylthio-2-methylpropanoyl)-L-phenylalanine and N-(3-mercapto-2-methylpropanoyl)-L-phenylalanine are obtained.

EXAMPLE 25

N-(3-Mercapto-2-methylpropanoyl)-L-threonine

By substituting L-threonine for the L-valine in the procedure of Example 22, and then treating the product by the procedure of Example 23, N-(3-acetylthio-2-methylpropanoyl)-L-threonine and N-(3-mercapto-2-methylpropanoyl)-L-threonine are obtained.

EXAMPLE 26

N-(3-Mercapto-2-methylpropanoyl)-L-glutamine

By substituting L-glutamine for the L-valine in the procedure of Example 22 and then treating the product by the procedure of Example 23, N-(3-acetylthio-2-methylpropanoyl)-L-glutamine and N-(3-mercapto-2-methylpropanoyl)-L-glutamine are obtained.

EXAMPLE 27

$N^{\alpha}$-(3-Mercapto-2-methylpropanoyl)-L-lysine

By substituting $N^{\epsilon}$-tert-butyloxycarbonyl-L-lysine for the L-valine in the procedure of Example 22, and then treating the product by the procedure of Example 23, $N^{\alpha}$-(3-acetylthio-2-methylpropanoyl)-$N^{\epsilon}$-tert-butyloxycarbonyl-L-lysine and $N^{\alpha}$-(3-mercapto-2-methylpropanoyl)-$N^{\epsilon}$-tert-butyloxycarbonyl-L-lysine are obtained. By treating these products with trifluoroacetic acid at room temperature for 15 minutes, $N^{\alpha}$-(3-acetylthio-2-methylpropanoyl)-L-lysine and $N^{\alpha}$-(3-mercapto-2-methylpropanoyl)-L-lysine are obtained.

EXAMPLE 28

N-(3-Mercapto-2-methylpropanoyl)-L-tyrosine

By substituting L-tyrosine for the L-valine in the procedure of Example 22, and then treating the product by the procedure of Example 23, N-(3-acetylthio-2-methylpropanoyl)-L-tyrosine and N-(3-mercapto-2-methylpropanoyl)-L-tyrosine are obtained.

EXAMPLE 29

N-(3-Mercapto-2-methylpropanoyl)-L-tryptophane

By substituting L-tryptophane for the L-valine in the procedure of Example 22, and then treating the product by the procedure of Example 23, N-(3-acetylthio-2-methylpropanoyl)-L-tryptophane and N-(3-mercapto-2-methylpropanoyl)-L-tryptophane are obtained.

EXAMPLE 30

N-(3-mercapto-2-methylpropanoyl)-L-methionine

By substituting L-methionine for the L-valine in the procedure of Example 22, and then treating the product by the procedure of Example 23, N-(3-acetylthio-2-methylpropanoyl)-L-methionine and N-(3-mercapto-2-methylpropanoyl)-L-methionine are obtained.

EXAMPLE 31

N-(3-Mercapto-2-methylpropanoyl)-N-methyl-L-phenylalanine

By substituting N-methyl-L-phenylalanine for the L-valine in the procedure of Example 22, and then treating the product by the procedure of Example 23, N-(3-acetylthio-2-methylpropanoyl)-N-methyl-L-phenylalanine and N-(3-mercapto-2-methylpropanoyl)-N-methyl-L-phenylalanine are obtained.

EXAMPLE 32

3-Acetylthio-2-benzylpropanoic acid chloride

2-Benzylacrylic acid (8.1 g.) and thiolacetic acid (5.3 g.) are mixed and heated on the steam bath for one hour. After cooling to room temperature, thionyl chloride (9.75 g.) is added and the mixture is stored overnight at room temperature. The excess thionyl chloride is removed in vacuo and the residue is distilled to obtain 3-acetylthio-2-benzylpropanoic acid chloride $b_{0.05}$:120°–122°.

EXAMPLE 33

$N^\alpha$-(3-Acetylthio-2-benzylpropanoyl)-L-arginine

By substituting 3-acetylthio-2-benzylpropanoic acid chloride for the 3-acetylthio-2-methylpropanoic acid chloride in the procedure of Example 20, $N^\alpha$-(3-acetylthio-2-benzylpropanoyl)-L-arginine, m.p. 253°–295°, is obtained.

EXAMPLE 34

$N^\alpha$-(3-mercapto-2-benzylpropanoyl)-L-arginine

By substituting $N^\alpha$-(3-acetylthio-2-benzylpropanoyl)-L-arginine for the $N^\alpha$-(3-acetylthio-2-methylpropanoyl)-L-arginine in the procedure of Example 21, $N^\alpha$-(3-mercapto-2-benzylpropanoyl)-L-arginine, m.p. 135°, is obtained.

EXAMPLES 35–48

By substituting the amino acid of column I for the L-alanine and chloroacetyl chloride for the 3-bromopropionyl chloride in the procedure of Example 1, then treating the product by the procedure of Example 22, the compounds of column II are obtained.

| Example | I | II |
|---|---|---|
| 35 | Glycine | N-2-Mercaptoacetylglycine |
| 36 | L-Alanine | N-2-Mercaptoacetyl-L-alanine |
| 37 | L-Valine | N-2-Mercaptoacetyl-L-valine |
| 38 | L-Leucine | N-2-Mercaptoacetyl-L-leucine |
| 39 | L-Serine | N-2-Mercaptoacetyl-L-serine |
| 40 | L-Asparagine | N-2-Mercaptoacetyl-L-asparagine |
| 41 | $N^\epsilon$-Boc-L-Lysine | $N^\alpha$-2-Mercaptoacetyl-$N^\epsilon$-Boc-L-lysine |
| 42 | L-Histidine | N-2-Mercaptoacetyl-L-histidine |
| 43 | L-Phenylalanine | N-2-Mercaptoacetyl-L-phenylalanine |
| 44 | L-Tryptophane | N-2-Mercaptoacetyl-L-tryptophane |
| 45 | L-Cysteine | N-2-Mercaptoacetyl-L-cysteine |
| 46 | L-Methionine | N-2-Mercaptoacetyl-L-methionine |
| 47 | Sarcosine | N-2-Mercaptoacetylsarcosine |
| 48 | N-methyl-L-Leucine | N-2-Mercaptoacetyl-N-Methyl-L-leucine |

EXAMPLE 49

$N^\alpha$-2-Mercaptoacetyl-L-lysine

By treating $N^\alpha$-2-mercaptoacetyl-$N^\epsilon$-Boc-L-lysine with trifluoroacetic acid at room temperature for 15 minutes, $N^\alpha$-2-mercaptoacetyl-L-lysine is obtained.

EXAMPLE 50

$N^\alpha$-2-Mercaptoacetyl-L-arginine

By substituting chloroacetyl chloride for the 3-bromopropionyl chloride in the procedure of Example 7, and treating the product by the procedure of Example 8, $N^\alpha$-2-benzoylthioacetyl-L-arginine and $N^\alpha$-2-mercaptoacetyl-L-arginine are obtained.

EXAMPLES 51–64

By substituting the amino acid of column I for the L-alanine and 2-bromopropionyl chloride for the 3-bromopropionyl chloride in the procedure of Example 1, then treating the product by the procedure of Example 2, the compounds of column II are obtained.

| Example | I | II |
|---|---|---|
| 51 | Glycine | N-2-Mercaptopropanoylglycine |
| 52 | L-Alanine | N-2-Mercaptopropanoyl-L-alanine |
| 53 | L-Valine | N-2-Mercaptopropanoyl-L-valine |
| 54 | L-Leucine | N-2-Mercaptopropanoyl-L-leucine |
| 55 | L-Serine | N-2-Mercaptopropanoyl-L-serine |
| 56 | L-Glutamine | N-2-Mercaptopropanoyl-L-glutamine |
| 57 | $N^\epsilon$-Boc-L-Lysine | $N^\alpha$-2-Mercaptopropanoyl-$N^\epsilon$-Boc-lysine |
| 58 | L-Histidine | N-2-Mercaptopropanoyl-L-histidine |
| 59 | L-Phenylalanine | N-2-Mercaptopropanoyl-L-phenylalanine |
| 60 | L-Tryptophane | N-2-Mercaptopropanoyl-L-tryptophane |
| 61 | L-Cysteine | N-2-Mercaptopropanoyl-L-cysteine |
| 62 | L-Methionine | N-2-Mercaptopropanoyl-L-methionine |
| 63 | Sarcosine | N-2-Mercaptopropanoylsarcosine |
| 64 | N-Methyl-L-Phenylalanine | N-2-Mercaptopropanoyl-N-methyl-L-phenylalanine |

EXAMPLE 65

$N^\alpha$-2-Mercaptopropanoyl-L-lysine

By treating $N^\alpha$-2-mercaptopropanoyl-$N^\alpha$-Boc-L-lysine with trifluoroacetic acid at room temperature for 15 minutes, $N^\alpha$-2-mercaptopropanoyl-L-lysine is obtained.

EXAMPLE 66

$N^\alpha$-2-Mercaptopropanoyl-L-arginine

By substituting 2-bromopropionyl chloride for the 3-bromopropionyl chloride in the procedure of Example 7 and then treating the product by the procedure of Example 8, $N^\alpha$-2-benzoylthiopropanoyl-L-arginine and $N^\alpha$-2-mercaptopropanoyl-L-arginine are obtained.

EXAMPLE 67

$N^\alpha$-4-Mercaptobutanoyl-L-arginine

By substituting 4-chlorobutyryl chloride for the 3-bromopropionyl chloride in the procedure of Example 7, and then treating the product by the procedure of Example 8, $N^\alpha$-4-benzoylthiobutanoyl-L-arginine and $N^\alpha$-4-mercaptobutanoyl-L-arginine are obtained.

The racemic forms of the final products in each of the foregoing examples are produced by utilizing the DL-form of the starting amino acid instead of the L-form.

Similarly the D-form of the final products in each of the foregoing examples is produced by utilizing the D-form of the starting amino acid instead of the L-form.

EXAMPLE 68

$N^\alpha$, $N^{\alpha'}$-[Dithio-3,3'-bis(2-methylpropanoyl)]-bis-L-arginine $N^\alpha$-(3-mercapto-2-methylpropanoyl)-L-arginine is dissolved in water and the pH is adjusted to 7 with N sodium hydroxide. A 0.5 M iodine solution in 95% ethanol is added dropwise while maintaining the pH between 6 and 7 by careful addition of N sodium hydroxide. When a permanent (5 minutes) yellow color is formed, the solution of iodine is stopped, the color is discharged by addition of sodium thiosulfate and the solution is concentrated to 1/10 of the original volume in vacuo. The resulting solution is applied to a column of ion exchange resin Dowex 50 and the $N^\alpha$-$N^{\alpha'}$-[dithio-3,3'-bis(2-methylpropanoyl)]-bis-L-arginine is eluted with pyridine acetate buffer, pH 6.5.

EXAMPLE 69

N-N'-[Dithio-3,3'-bis(2-methylpropanoyl)]-bis-L-valine

N-(3-mercapto-2-methylpropanoyl)-L-valine is dissolved in water and the pH is adjusted to 7 with N-sodium hydroxide. A 0.5 M iodine solution in 95% ethanol is added dropwise while maintaining the pH between 6 and 7 by careful addition of N-sodium hydroxide. When a permanent (5 minutes) yellow color is obtained, the addition of iodine is discontinued and the yellow color is discharged with sodium thiosulfate. The aqueous alcoholic solution is acidified with N hydrochloric acid and the N-N'-[dithio-3,3-bis-(2-methylpropanoyl)]-bis-L-valine is extracted with ethyl acetate.

EXAMPLE 70

N-(3-Mercaptopropanoyl)-N-benzylglycine

By substituting N-benzylglycine for the L-alanine in the procedure of Example 1, and then treating the product by the procedure of Example 2, N-(3-benzoylthiopropanoyl)-N-benzylglycine and N-(3-mercaptopropanoyl)-N-benzylglycine are obtained.

EXAMPLE 71

N-(3-Mercaptopropanoyl)-N-benzyl-L-leucine

By substituting N-benzyl-L-leucine for the L-alanine in the procedure of Example 1, and then treating the product by the procedure of Example 2, N-(3-benzoylthiopropanyl)-N-benzyl-L-leucine and N-(3-mercaptopropanoyl)-N-benzyl-L-leucine are obtained.

EXAMPLE 72

N-(3-Mercaptopropanoyl)-L-aspartic acid

By substituting L-aspartic acid for L-alanine in the procedure of Example 1, and then treating the product by the procedure of Example 2, N-(3-benzoylthiopropanoyl)-L-aspartic acid and N-(3-mercaptopropanoyl)-L-aspartic acid are obtained.

EXAMPLE 73

N-(DL-3-Acetylthio-2-methylpropanoyl)-L-tyrosine

L-tyrosine (2.718 g.) is suspended in 17.6 ml. of 0.85 N sodium hydroxide with stirring in an ice bath. 7.5 ml. of 2 N sodium hydroxide is added, followed immediately by 2.7 g. of 3-acetylthio-2-methylpropanoyl chloride and 5 ml. of ether. After four hours, the mixture is diluted with water to 300 ml. and extracted twice with ethyl acetate. The aqueous phase is acidified with concentrated hydrochloric acid and thoroughly extracted with ethyl acetate. The crude product, N-(DL-3-acetylthio-2-methylpropanoyl)-L-tyrosine, is chromatographed on silica gel with benzene-acetic acid (7:3), yield 1.6 g.

EXAMPLE 74

N-(DL-3-Mercapto-2-methylpropanoyl)-L-tyrosine

N-(DL-3-acetylthio-2-methylpropanoyl)-L-tyrosine (1.1 g.) is taken up in methanol with stirring under an argon blanket and treated with 10 ml. concentrated ammonium hydroxide. After 30 minutes, the methanol is removed in vacuo. The aqueous mixture is extracted with ethyl acetate and acidified with 10% potassium bisulfate. The ethyl acetate extract is washed with water, dried over magnesium sulfate and concentrated to dryness in vacuo. The product, N-(DL-3-mercapto-2-methylpropanoyl)-L-tyrosine is purified by chromatography on a silica gel column with benzene-acetic acid (7:3), yield 394 mg., $[\alpha]_D = 25.9°$ (c = 1.95, methanol).

EXAMPLE 75

3-Hydroxy-N-(DL-3-acetylthio-2-methylpropanoyl)-L-tyrosine 3-(3,4-Dihydroxyphenyl)-L-alanine (3.94 g.) is taken up in 23.6 ml. of 0.85 N sodium hydroxide with stirring in an ice bath under argon. 10 ml. of 2 N sodium hydroxide is added, followed immediately by 3.6 g. of 3-acetylthio-2-methylpropanoyl chloride in 10 ml. of ether. The ice bath is removed after one hour. A precipitate forms then 30 ml. of water are added. After four hours, the mixture is acidified with concentrated hydrochloric acid and extracted with ethyl acetate to obtain 5.8 g. of crude 3-hydroxy-N-(DL-3-acetylthio-2-methylpropanoyl)-L-tyrosine.

EXAMPLE 76

3-Hydroxy-N-(DL-3-mercapto-2-methylpropanoyl)-L-tyrosine

3-Hydroxy-N-(DL-3-acetylthio-2-methylpropanoyl)-L-tyrosine (4.9 g.) is suspended in 20 ml. of water in an ice bath under argon. 20 ml. of concentrated ammonium hydroxide are added. After 30 minutes at room temperature the mixture is chilled, acidified with concentrated hydrochloric acid and then extracted with ethyl acetate. The crude product (4.4 g.) is taken up in chloroform-acetic acid (7.3) and chromatographed on a column of silica gel wrapped in aluminum foil. The product, 3-hydroxy-N-(DL-3-mercapto-2-methylpropanoyl)-L-tyrosine, is eluted with chloroform-acetic acid, and the fractions are worked up in a darkened laboratory, yield 2.9 g., $[\alpha]_D = 23.5$ (c = 1,86, methanol), $R_f = 0.46$. A small aliquot is converted to the t-butylamine salt with t-butylamine in ethyl acetate.

EXAMPLE 77

3-Hydroxy-N-(3-acetylthiopropanoyl)-L-tyrosine 3-(3,4-Dihydroxyphenyl)-L-alanine (1.97 g.) and 3-acetylthiopropanoyl chloride (1.66 g.) are made to react according to the procedure of Example 75. The crude ethyl acetate extract (1.85 g.) is taken up in chloroform-acetic acid (7:3) and chromatographed on a silica gel column, eluting with chloroform-acetic acid (6:4), concentrated to dryness, taken up in water and lyophilized to obtain 317 mg. of 3-hydroxy-N-(3-acetylthiopropanoyl)-L-tyrosine.

EXAMPLE 78

3-Hydroxy-N-(3-mercaptopropanoyl)-L-tyrosine

3-Hydroxy-N-(3-acetylthiopropanoyl)-L-tyrosine (280 mg.) is treated with concentrated ammonium hydroxide according to the procedure in Example 76. The crude product, 3-hydroxy-N-(3-Mercaptopropanoyl)-L-tyrosine is crystallized from acetonitrile, yield 157 mg., m.p. 89°–91°.

EXAMPLE 79

1000 tablets each containing 100 mg. of N-(3-mercaptopropanoyl)-L-phenylalanine are produced from the following ingredients:

| | |
|---|---|
| N-(3-mercaptopropanoyl)-L-phenylalanine | 100 g. |
| Corn starch | 50 g. |
| Gelatin | 7.5 g. |
| Avicel (microcrystalline cellulose) | 25 g. |
| Magnesium stearate | 2.5 g. |

The N-(3-mercaptopropanoyl)-L-phenylalanine and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 mg. of active ingredient.

EXAMPLE 80

1000 tablets each containing 200 mg. of N-2-mercaptopropanoylglycine are produced from the following ingredients:

| | |
|---|---|
| N-2-mercaptopropanoylglycine | 200 g. |
| Lactose | 100 g. |
| Avicel | 150 g. |
| Corn starch | 50 g. |
| Magnesium stearate | 5 g. |

The N-2-mercaptopropanoylglycine, lactose and Avicel are admixed, then blended with the corn starch. Magnesium stearate is added. The dry mixture is compressed in a tablet press to form 1000 505 mg. tablets each tablet containing 200 mg. of active ingredient. The tablets are coated with a solution of Methocel E 15 (methyl cellulose) including as a color a lake containing yellow #6.

EXAMPLE 81

An injectable solution is produced as follows:

| | |
|---|---|
| N-(3-mercaptopropanoyl)-L-phenylalanine | 500 g. |
| Methyl paraben | 5 g. |
| Propyl paraben | 1 g. |
| Sodium chloride | 25 g. |
| Water for injection qs. | 5 l |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

EXAMPLE 82

Although conversion of angiotensin I to angiotensin II by angiotensin-converting enzyme is probably the reaction of most importance in the pathology of hypertension, the activity of the isolated enzyme is more conveniently and accurately assayed by measuring its rate of cleavage of a simpler peptide substrate, hippuryl-L-histidyl-L-leucine. For determination of $I_{50}$ values (concentrations of compounds expressed in micrograms/ml producing a 50% inhibition of angiotensin-converting enzyme) various concentrations of each compound are added to 13×100 mm tubes along with the following components at the indicated final concentrations in a final volume of 0.25 ml: 100 mM potassium phosphate buffer, pH 8.3; 300 mM sodium chloride; 5 mM hippuryl-L-histidyl-L-leucine; and 5 milliunits of angiotensin-converting enzyme of rabbit lung. Controls containing no inhibitor (100% activity), and those acidified before addition of the enzyme (0% activity) are similarly prepared. All of the enzymatic reactions are initiated by addition of the enzyme component; tubes are incubated for 30 minutes at 37° C.; and reactions are terminated by addition of 0.25 ml. of 1 N HCl. The hippuric acid formed by action of angiotensin-converting enzyme on hippuryl-L-histidyl-L-leucine is extracted into ethyl acetate, evaporated to dryness, redissolved in water and quantitated from its absorbance at 228 nm. The percent inhibition by each concentration of compound is calculated by comparison with the 0% and 100% activity controls. The concentrations of representative compounds of the present invention which inhibit activity of angiotension-converting enzyme by 50% are shown in the following table:

| Compound of Example | I$_{50}$ (μg/ml) |
|---|---|
| 2 | 1.2 |
| 4 | 1.8 |
| 6 | 0.86 |
| 8 | 0.17 |
| 10 | 1.8 |
| 15 | 2.0 |
| 51 | 2.6 |

EXAMPLE 83

The procedure for evaluating the inhibition of angiotensin I converting enzyme in excised guinea pig ileum is carried out as follows: varying concentrations of the compound are added to an excised guinea pig ileum bath in Krebs solution at 37°, aerated with a mixture of 95% $O_2$–5% $CO_2$. After two minutes, angiotensin I (25 ng/ml) is added and the isotonic contractions are measured. The concentration of representative compounds of the present invention (in micrograms/ml) which inhibit the contractile activity of angiotensin I by 50% (IC$_{50}$) are shown in the following table:

| Compound of Example | IC$_{50}$ (μg/ml) |
|---|---|
| 2 | 0.94 |
| 4 | 2.0 |
| 6 | 0.52 |
| 8 | 0.9 |
| 10 | 0.94 |
| 15 | 4.5 |
| 34 | 4.1 |
| 51 | 2.0 |

EXAMPLE 84

Representative compounds of the present invention are administered orally to unanesthetized male rats of the Sprague-Dawley strain, weighing about 200 g., followed by an injection of 0.31 μg/kg of angiotensin I. The following table indicates the degree of inhibition obtained.

| Compound of Example | Dose mg/kg | No. of animals | % maximum inhibition of angiotensin I pressor response ± SE |
|---|---|---|---|
| 15 | 10 | 2 | 34.2 ± 6.7% |
|  | 100 | 2 | 61.5 ± 1.2% |
| 51 | 10 | 2 | 29.9 ± 3.1% |
|  | 30 | 2 | 52.9 ± 15.8% |
|  | 100 | 2 | 64.9 ± 12.3% |

EXAMPLE 85

Male rats of the CF Nelson strain are anesthetized with ether and each left renal artery is partially constricted with a silver clip (i.d. 0.22 mm). The right kidney and renal artery are left intact. This model, which is commonly designated as the "2-kidney Goldblatt renal hypertensive rat", has been considered typical of renin-angiotensin dependent hypertension [(Gavras, et al., Science 188, 1316 (1975)]. The abdominal aortas are cannulated 5 weeks after clipping the left renal artery. One week after cannulation mean blood pressures and heart rates are recorded directly for 4–8 hours during which time the rats are dosed orally every 24 hours for two consecutive days with 300 mg. of the compound of Example 51. The following table shows the lowering of blood pressure in two different rats at the second dosage day.

|  | Mean blood pressure mm Hg. | |
|---|---|---|
|  | Rat #9 | Rat #10 |
| Before drug administration | 222 | 206 |
| After drug administration |  |  |
| 1 h | 206 | 203 |
| 2 h | 173 | 190 |
| 3 h | 157 | 189 |
| 4 h | 184 | 199 |
| 5 h | 206 | 195 |
| 6 h | 199 | 197 |

When the same dose is administered orally to a normotensive rat no significant effects on blood pressure are observed.

What is claimed is:

1. A compound of the formula

or a physiologically acceptable salt thereof, wherein
R$_1$ is hydroxy-lower alkylene, hydroxyphenyl-lower alkylene, amino-lower alkylene, guanidino-lower alkylene, mercapto-lower alkylene, lower alkylmercapto-lower alkylene, carbamoyl-lower alkylene or carboxy-lower alkylene;
R$_2$ and R$_3$ each is hydrogen, lower alkyl or phenyl-lower alkylene; and
R$_5$ is hydrogen, lower alkanoyl, benzoyl or

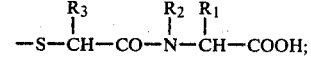

with the proviso that if R$_2$ and R$_5$ are both hydrogen and R$_3$ is methyl, R$_1$ is not mercapto-lower alkylene.

2. A compound of the formula

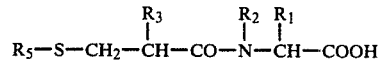

or a physiologically acceptable salt thereof, wherein
R$_1$ is lower alkyl, phenyl-lower alkylene, hydroxy-lower alkylene, hydroxyphenyl-lower alkylene, amino-lower alkylene, guanidino-lower alkylene, mercapto-lower alkylene, lower alkylmercapto-lower alkylene, carbamoyl-lower alkylene or carboxy-lower alkylene;
R$_2$ and R$_3$ each is hydrogen, lower alkyl or phenyl-lower alkylene; and
R$_5$ is hydrogen, lower alkanoyl, benzoyl or

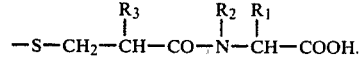

3. A compound of the formula

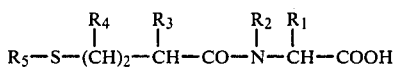

or a physiologically acceptable salt thereof, wherein

R₁ is hydrogen, lower alkyl, phenyl-lower alkylene, hydroxy-lower alkylene, hydroxyphenyl-lower alkylene, amino-lower alkylene, guanidino-lower alkylene, mercaptolower alkylene, lower alkylmercapto-lower alkylene, carbamoyllower alkylene, or carboxy-lower alkylene;

R₂, R₃ and R₄ each is hydrogen, lower alkyl or phenyl-lower alkylene; and

R₅ is hydrogen, lower alkanoyl, benzoyl or

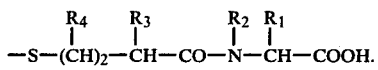

4. A compound as in claim 2 wherein R₁ is guanidino-lower alkylene, amino-lower alkylene, phenyl-lower alkylene or lower alkyl; R₂ and R₅ each is hydrogen; and R₃ is hydrogen, lower alkyl or phenyl-lower alkylene.

5. A compound as in claim 2 wherein R₁ is guanidinopropyl, aminopropyl, aminobutyl, phenylmethyl, or isobutyl; R₂ and R₅ each is hydrogen; and R₃ is hydrogen, lower alkyl or phenyl-lower alkylene.

6. A compound as in claim 2 wherein R₁ is phenylmethyl and R₂, R₃ and R₅ each is hydrogen.

7. A compound as in claim 2 wherein R₁ is isobutyl and R₃ is hydrogen.

8. A compound as in claim 2 wherein R₁ is guanidinopropyl and R₂, R₃ and R₅ each is hydrogen.

9. A compound as in claim 2 wherein R₅ is

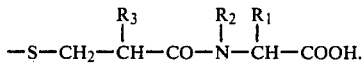

10. A compound as in claim 9 wherein each R₁ is guanidinopropyl.

11. A compound as in claim 9 wherein each R₁ is isopropyl.

12. A compound as in claim 6 wherein R₂ and R₅ each is hydrogen having the name N-(3-mercaptopropanoyl)-L-phenylalanine.

13. A compound as in claim 7 wherein R₂ and R₅ each is hydrogen having the name N-(3-mercaptopropanoyl)-L-leucine.

14. A compound as in claim 8, wherein R₂ and R₅ each is hydrogen having the $N^\alpha$-(3-mercaptopropanoyl)-L-arginine.

15. A compound as in claim 2 wherein R₁ is guanidinopropyl, R₂ and R₅ each is hydrogen and R₃ is methyl having the name $N^\alpha$-(3-mercapto-2-methylpropanoyl)-L-arginine.

16. A compound as in claim 10 wherein each R₂ is hydrogen and each R₃ is methyl, having the name $N^\alpha$, $N^{\alpha'}$-[dithio-3,3'-bis(2-methylpropanoyl)]-bis-L-arginine.

17. A compound as in claim 11 wherein each R₂ is hydrogen and each R₃ is methyl having the name N,N'-[dithio-3,3'-bis(2-methylpropanoyl)]-bis-L-valine.

18. A compound as in claim 2 wherein R₁ is hydroxyphenyl-lower alkylene.

19. A compound as in claim 2 wherein R₁ is (4-hydroxyphenyl)methyl, R₂ and R₅ each is hydrogen and R₃ is methyl having the name N-(3-mercapto-2-methylpropanoyl)-L-tyrosine.

20. A compound as in claim 2 wherein R₁ is (3,4-dihydroxyphenyl)methyl, R₂ and R₅ each is hydrogen and R₃ is methyl having the name 3-hydroxy-N-(DL-3-mercapto-2-methylpropanoyl)-L-tyrosine.

21. A compound as in claim 2 wherein R₁ is (3,4-dihydroxyphenyl)methyl and R₂, R₃ and R₅ each is hydrogen having the name 3-hydroxy-N-(3-mercaptopropanoyl)-L-tyrosine.

* * * * *

UNITED STATES PATENT AND TRADEMARK OFFICE
CERTIFICATE OF CORRECTION

PATENT NO. : 4,339,600
DATED : July 13, 1982
INVENTOR(S) : Miguel A. Ondetti, et al.

It is certified that error appears in the above—identified patent and that said Letters Patent is hereby corrected as shown below:

Column 3, lines 30 and 31, delete the word "leucine", both occurrences.

Signed and Sealed this

Eighteenth Day of January 1983

[SEAL]

Attest:

GERALD J. MOSSINGHOFF

Attesting Officer

Commissioner of Patents and Trademarks